(12) United States Patent
Richard et al.

(10) Patent No.: US 8,871,677 B2
(45) Date of Patent: Oct. 28, 2014

(54) MULTI-LOBED POROUS CERAMIC BODY AND PROCESS FOR MAKING THE SAME

(75) Inventors: Michael A. Richard, Fulshear, TX (US); John David Covey, College Station, TX (US)

(73) Assignee: Saint-Gobain Ceramics & Plastics, Inc., Worcester, MA (US)

( * ) Notice: Subject to any disclaimer, the term of this patent is extended or adjusted under 35 U.S.C. 154(b) by 0 days.

(21) Appl. No.: 13/316,783

(22) Filed: Dec. 12, 2011

(65) Prior Publication Data
US 2012/0171407 A1 Jul. 5, 2012

Related U.S. Application Data

(60) Provisional application No. 61/428,009, filed on Dec. 29, 2010.

(51) Int. Cl.
| | | |
|---|---|---|
| B01J 23/02 | (2006.01) | |
| B01J 23/10 | (2006.01) | |
| B01J 23/48 | (2006.01) | |
| B01J 23/50 | (2006.01) | |
| B01J 35/00 | (2006.01) | |
| B01J 35/02 | (2006.01) | |
| B01J 35/04 | (2006.01) | |
| B01J 35/10 | (2006.01) | |
| C07D 301/08 | (2006.01) | |
| C07C 213/04 | (2006.01) | |
| B01J 37/02 | (2006.01) | |
| B01J 23/68 | (2006.01) | |

(52) U.S. Cl.
CPC ............ *C07D 301/08* (2013.01); *C07C 213/04* (2013.01); *B01J 37/024* (2013.01); *B01J 23/688* (2013.01); *B01J 35/00* (2013.01); *B01J 3/1009* (2013.01); *B01J 35/1038* (2013.01); *B01J 35/109* (2013.01); *B01J 37/0201* (2013.01)
USPC ............................ 502/439; 502/347; 549/534

(58) Field of Classification Search
None
See application file for complete search history.

(56) References Cited

U.S. PATENT DOCUMENTS

| | | | |
|---|---|---|---|
| 7,169,736 B2 | 1/2007 | Petrolli et al. | |
| 2003/0162655 A1* | 8/2003 | Szymanski et al. ........... | 502/243 |
| 2004/0043900 A1* | 3/2004 | Combs .......................... | 502/439 |
| 2009/0131695 A1 | 5/2009 | Gerdes | |
| 2009/0306410 A1 | 12/2009 | Brandstaedter et al. | |

FOREIGN PATENT DOCUMENTS

WO 2010047949 A1 4/2010

* cited by examiner

*Primary Examiner* — Melvin C Mayes
*Assistant Examiner* — Colin W Slifka
(74) *Attorney, Agent, or Firm* — Stewart A. Fraser

(57) ABSTRACT

A carrier having at least three lobes, a first end, a second end, a wall between the ends and a non-uniform radius of transition at the intersection of an end and the wall is disclosed. A catalyst comprising the carrier, silver and promoters deposited on the carrier and useful for the epoxidation of olefins is also disclosed. A method for making the carrier, a method for making the catalyst and a process for epoxidation of an olefin with the catalyst are also disclosed.

24 Claims, 4 Drawing Sheets

MULTI-LOBED POROUS CERAMIC BODY AND PROCESS FOR MAKING THE SAME

CROSS-REFERENCE TO RELATED APPLICATION

This application claims the benefit of U.S. Provisional Application No. 61/428,009 filed Dec. 29, 2010.

BACKGROUND OF THE INVENTION

This invention relates to porous ceramic bodies having a contoured shape that is particularly suitable for use as a carrier for catalytically active material. The combination of carrier and active material may function as a catalyst when randomly disposed within a reactor tube which is useful in the manufacture of chemicals such as ethylene oxide.

Ethylene oxide, which may be abbreviated herein as EO, is an important industrial chemical used as a feedstock for making such chemicals as ethylene glycol, ethylene glycol ethers, alkanol amines and detergents. One method of manufacturing ethylene oxide is by the catalyzed partial oxidation of ethylene with oxygen. There are continuing efforts to develop catalysts that can improve the operating efficiency of such ethylene oxide manufacturing processes. Some of the desirable properties of an ethylene oxide catalyst include good selectivity, good activity, and long catalyst life. It is also important that the catalyst as loaded in the reactor tubes results in as relatively low pressure drop across the EO reactor as is possible. Achieving significant pressure drop improvement with higher packing density would enhance the stability of an EO catalyst in existing EO plants and would allow for the design of more efficient new EO plants.

The typical catalysts employed to make EO comprise silver and other metals and promoters on a carrier, typically an alpha alumina carrier. These silver catalysts are described in many US and foreign patents, including, among others, U.S. Pat. No. 4,242,235; U.S. Pat. No. 4,740,493; U.S. Pat. No. 4,766,105; U.S. Pat. No. 7,507,844; U.S. Pat. No. 7,507,845; U.S. Pat. No. 7,560,577; U.S. Pat. No. 7,560,411; U.S. Pat. No. 7,714,152; US 2008/0081920; US 2008/0306289; US 2009/0131695 and US 2009/0198076. The shape of the catalyst takes the shape of the carrier. The shape of a carrier may be characterized by describing one or more of the following features: length, outer diameter, inner diameter; ratio of length to diameter; radius of an exterior wall; radius of an end surface; shape when viewed from an end; and shape when viewed from a side. The most common commercially available carrier shape is a small cylinder pellet shape with a hole in the center of the pellet. See, e.g., U.S. Pat. No. 7,259,129, which disclosure is herein incorporated by reference. In the '129 patent the support material has to specific physical properties and is preferably formed into a shaped agglomerate of the support material having a hollow cylinder geometric configuration or structure with a relatively small internal diameter. In contrast, U.S. Pat. No. 4,441,990 discloses hollow shaped catalytic extrudates which may be employed in catalytically promoted processes including hydrocarbon processing operations. The shapes include essentially rectangular shaped tubes, and triangular shaped tubes in cross section. One embodiment is characterized by having bulbous protrusions around the external periphery. Wall thicknesses from about ⅛ inch, 1/10 inch, or even 1/25 inch or less are disclosed. US 2009/0227820 discloses a geometrically shaped refractory solid carrier in which at least one wall thickness of the carrier is less than 2.5 mm U.S. Pat. No. 6,518,220 discloses shaped catalysts for heterogeneously catalyzed reactions in the form of hollow cylinders or annular tablets whose end faces are rounded both to the outer edge and to the edge of the central hole, so that they have no right-angled edges. One modification of such a catalyst shape comprises a pellet where the rounded edges are only on the outer edge of the pellet, and the inner edge of the central hole does not comprise rounded edges. U.S. Pat. No. 6,325,919 discloses catalyst carriers composed of a refractory inorganic oxide having a rotationally symmetrical shape having a hollow portion, such as a doughnut shape. An outer peripheral surface and the inner peripheral surface separating the hollow portion are linked by curved surfaces, and the height of the carrier along the rotational symmetry axis is less than the outer diameter of the carrier. EP 1,184,077 discloses a porous refractory carrier in the form of an angular extrudate with rounded edges. WO 03/013725 discloses elongated shaped trilobal particles. U.S. Pat. No. 2,408,164 discloses numerous shaped catalyst including planar, cylindrical with a central opening and a plurality of parallel grooves disposed in the outer periphery, and cylindrical with several parallel passageways formed therein. U.S. Pat. No. 4,645,754 discloses catalysts made from a carrier that is in the shape of Intalox saddles or Berl saddles. Other shapes that have been mentioned in the patent art include spheres, tablets, rings, spirals, pyramids, cylinders, prisms, cuboids, cubes, etc. See, for example: US Published Patent Applications 2008/0015393, 2008/0255374, 2009/0041751, 2009/0227820; U.S. Pat. Nos. 5,155,242 and 7,547,795; and international publication WO 2004/014549.

However, there continues to be a need for improved catalysts having better performance in the reactor than currently are available. The present invention provides carriers and catalysts that enable such an improvement.

SUMMARY

A carrier of the present invention provides for improved performance in a reactor by combining a multi-lobal cross-sectional configuration with non-uniform rounding at the intersections of the carrier's ends and wall. A catalyst of the present invention is a novel combination of catalytic components and a carrier of this invention.

In one embodiment, this invention is a porous ceramic body comprising a first end, a second end, and a wall disposed between the ends. The wall comprises at least three lobes formed in the length of the wall. The first end and wall intersect one another at a first circumferential line having a non-uniform radius of transition.

In another embodiment, the invention is a catalyst that includes silver and promoters useful for the epoxidation of ethylene deposited on a specifically shaped porous ceramic body having a first end, a second end, and a wall disposed between the ends. The wall comprises at least three lobes formed in the length of the wall. The first end and wall intersect one another at a first circumferential line having a non-uniform radius of transition.

According to another aspect of the invention, a method is provided for making the catalyst of this invention. Suitably, the method involves providing a carrier of this invention and impregnating the carrier with a silver-containing solution such that the amount of silver metal on the carrier exceeds 8 weight percent of the weight of the catalyst. Preferred amounts of silver are between 10 and 30 weight percent of the weight of the catalyst. The silver impregnated shaped carrier is then heat treated to provide the catalyst, for example in a temperature range of from 100° to 500° C., preferably from 150° to 320° C.

According to yet another aspect of the invention, a packed catalyst bed is provided which is formed from catalyst particles comprising silver supported on a carrier of this invention, which catalyst bed has a silver loading of at least 50 kg silver/m$^3$ of catalyst bed.

According to yet another aspect of the invention, the catalyst made by the above-described method, or the above described catalyst bed is used in a process for manufacturing ethylene oxide by contacting the catalyst, under suitable epoxidation process conditions, with a feed stream that comprises ethylene and oxygen.

Further, the invention provides a method of using ethylene oxide for making ethylene glycol, an ethylene glycol ether or an 1,2-alkanolamine comprising converting ethylene oxide into ethylene glycol, the ethylene glycol ether, or the 1,2-alkanolamine, wherein the ethylene oxide has been obtained by the process for preparing ethylene oxide according to this invention.

DETAILED DESCRIPTION

As used herein, the phrases "porous ceramic body", "carrier" and "support" are used interchangeably. The word "catalyst" refers to a carrier that includes a catalytically active material deposited onto the carrier. Because the thickness of the catalytically active material is very small relative to the width of the carrier, the apparent shape of the carrier and the shape of the catalyst are essentially identical.

A "porous ceramic body" may refer to an elongated rod like body having a multi-lobal cross sectional shape—i.e., when viewed from either end, the end faces of the porous body have a multi-lobal shape and the body has a certain height which may also be described as its length. Examples of multi-lobal shaped carriers are shown, for example, in FIGS. 8A to 8J. One embodiment of a multi-lobal porous ceramic body is a hollow quadrilobal shaped carrier. The phrase "quadrilobal shaped" refers to the carrier's cross-sectional view having four non-triangularly, for example semi-circularly, shaped extensions on the circumference thereof. Perspective views of hollow quadrilobal shaped carriers are shown, for example, in FIGS. 1 and 5B. The phrase "hollow quadrilobal shaped object" refers to a cross-section having at least one passageway therethrough, with four non-triangularly, for example semi-circularly, shaped extensions on the circumference thereof.

Figure 4A:
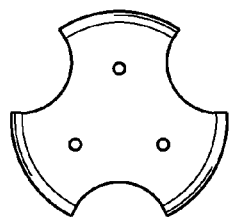
FIGS. 4A and 4B depict an end view and a perspective view of a third embodiment of a carrier of this invention.

Porous ceramic bodies used as carriers for catalytically active material have numerous physical and chemical characteristics that collectively and individually influence the selectivity, longevity, yield and durability of the catalyst when disposed in a chemical reactor. The porous body's physical and chemical characteristics may also impact the manufacturability of the carrier and the catalyst. Numerous patents and technical articles have focused on improving the catalyst by modifying characteristics such as the carrier's surface area, pore size distribution and morphology, which may be referred to herein as the carrier's micro physical characteristics. In other publications, the carrier's macro physical characteristics, such as its length, outer diameter and inner diameter, have been described. In yet other publications, the relationships between the carrier's macro physical characteristics and the reactor tube's inside diameter have been described. The inventor of the invention claimed herein has discovered that the total performance of the catalyst, which includes: preparation of the carrier and preparation of the catalyst; selectivity and longevity of the catalyst; pressure drop within the reactor; and the carrier's resistance to attrition and breakage, may all be favorably influenced by shaping the carrier to include multiple lobes and rounded corners having a non-uniform radius of transition. The combination of rounded corners and multiple lobes may be used to increase the packing density of the catalyst in the reactor relative to conventional carrier rings with non-rounded corners. An increase in packing density may be significant because the quantity of silver per unit volume of the reactor increases as the packing density of the carrier increases. Increasing the quantity of silver per unit volume of the reactor may improve the reactor's throughput which may be referred to herein as the yield. Furthermore, the combination of rounded corners and multiple lobes may also cooperate to provide less tortuous passageways for the flow of fluids through the catalyst bed in the reactor, relative to a bed of carrier rings with non-rounded corners, which avoids a significant increase in pressure drop despite the increase in the catalyst's packing density. The combination of rounded corners and multiple lobes also eliminates the portions of the catalyst that are most readily attrited during the procedures used to manufacture the catalyst. Minimizing both the pressure drop in the reactor and the amount of attrited particles while increasing the catalyst's packing density allows the potential impact of the carrier's micro physical characteristics to be more fully utilized thereby resulting in improved selectivity and longevity which collectively improve the reactor's economic performance. In addition to characteristics that enhance the selectivity to and longevity of the catalyst, the carrier should also have sufficient mechanical strength to prevent breaking during the catalyst manufacturing process and the process of loading the catalyst into the reactor. In some embodiments, the carrier has at least one passageway disposed through the length of the carrier. In some embodiments the carrier may have 2 to 4 passageways. In some embodiments the carrier may have one passageway for each lobe. If the carrier has an even number of lobes, the carrier may have an even number of passageways. Similarly, if the carrier has an odd number of lobes, the carrier may have an odd number of passageways. Furthermore, the number of lobes and the number of passageways do not need to be the same. The passageways may be symmetrically or asymmetrically disposed about the carrier's central axis which, by definition, extends from the carrier's first end to its second end and is located at the center of the carrier. One of the advantages of a hollow "multi-lobal" shaped carrier is that the carrier may have good mechanical strength, which may be quantified by measuring the carrier's side crushing strength (SCS) and its bulk crushing strength (BCS), despite the presence of a passageway through the catalyst. The use of multiple passageways may be preferred to the use of a single passageway that has the same cross-sectional surface area as the multiply passageways combined, because the multiple passageways provide for a smaller wall thickness and thus minimize the impact of diffusion limitations through the carrier. Still further, catalyst with multiple passageways may also be easier to manufacture than catalyst with a single opening. In one embodiment and as shown in FIG. 4A, the carrier is a trilobal shape wherein the lobes are truncated on the outer portion of the lobes and the number of passageways is equal to the number of lobes.

Features and characteristics of the carriers and catalysts of this invention, and the methods to manufacture the same, will now be described.

Figure 1:
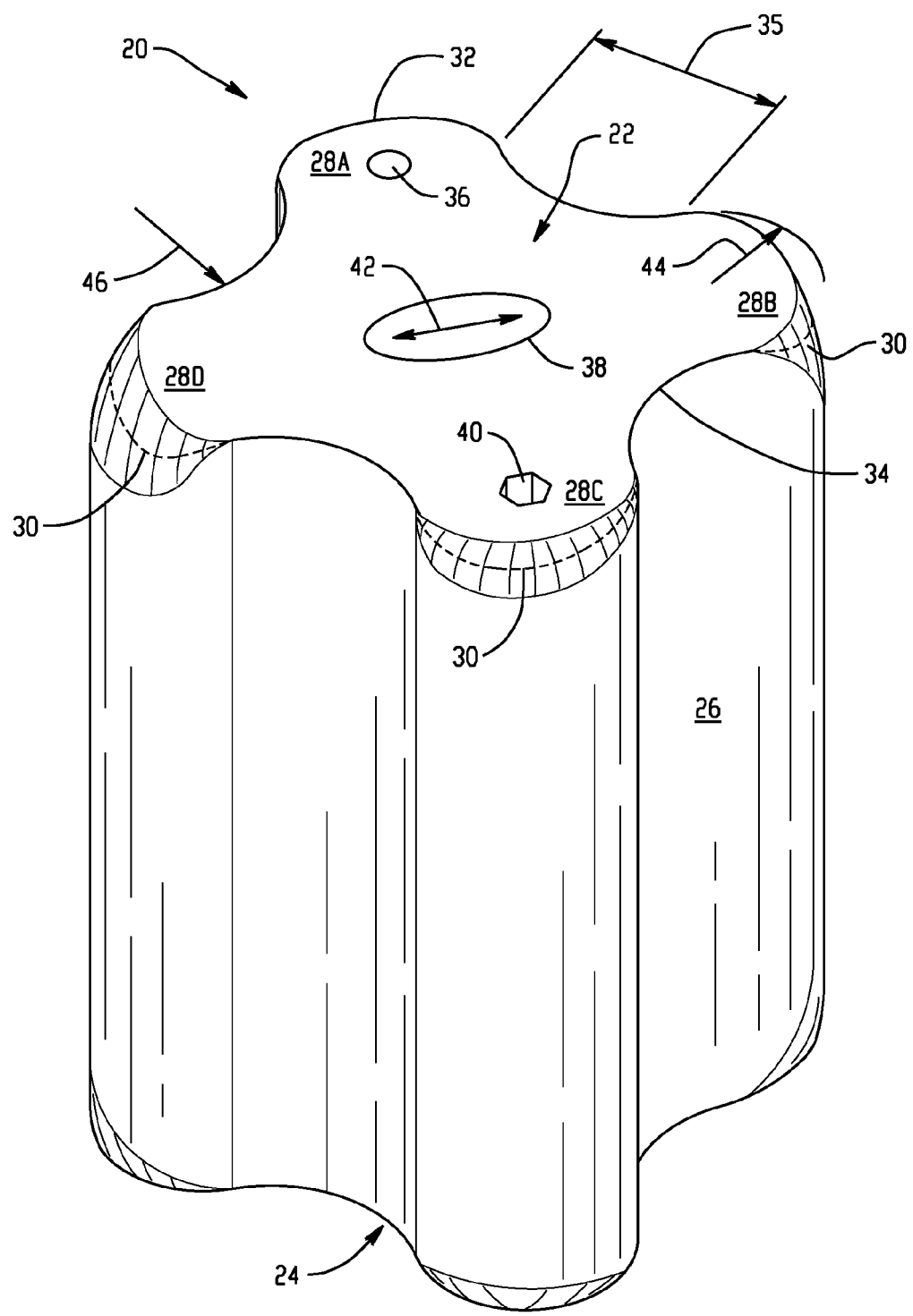
FIG. 1 is a perspective view of a first embodiment of a carrier of this invention.

Shown in FIG. 1 is a quadrilobal carrier 20, which may also be described herein as a quadrilobate carrier that includes first end 22, second end 24 and wall 26. Carrier 20 includes first lobe 28A, second lobe 28B, third lobe 28C and fourth lobe 28D. The intersection of first end 22 and wall 26 form first circumferential to line 30 which is denoted by the dotted line in FIG. 1. The first circumferential line is defined as a continuous series of points around the carrier where the surface of first end 22 transitions to the surface of wall 26. The radii of transition from the first end to the wall is non-uniform along the circumferential line because the transition from the first end to the wall has been rounded more in some locations and not rounded or rounded very little in other locations thereby creating the non-uniform radius of transition along the circumferential line. The largest radii of transition is at apex 32 of each of the lobes and the smallest radii of transition is at nadir 34 in the valleys 35 formed between two lobes. Between one of the largest radii of transition and an adjoining smallest radii of transition the radii of transition varies along the circumferential line. Carrier 20 includes first passageway 36, second passageway 38 and third passageway 40. Each passageway extends completely through the carrier thereby allowing fluids, including liquids used in the catalyst preparation process and gases used in a reactor tube, to flow into and through the carrier from one end of the carrier to the opposite end of the carrier. First passageway 36 is circular. Second passageway 38 is oval shaped and the longest axis 42 of the oval aligns with the apexes of lobes 28B and 28D. Third passageway 28C is a six sided polygon. The radius of lobe 28B is identified by arrow 44 and the radius of the valley between lobes 28A and 28D is identified by arrow 46. Although not shown in FIG. 1, second end 24 intersects wall 26 at a second circumferential line which is defined as a continuous series of points around the carrier where the surface of second end 24 transitions to the surface of wall 26.

To determine the radius of transition for the leading edge of a carrier's lobe, an optical comparator can be used to illuminate the carrier thereby creating an image that can be measured. However, to determine the minimum radius of transition at a carrier's valley, the carrier can be cross sectioned to expose the valley and the radius can be measured using an optical comparator.

As used herein, a carrier is considered to have a non-uniform radius of transition if a carrier's largest radius of transition at the intersection of the wall to and end is at least three times greater than the carrier's smallest radii of transition at the intersection of the same wall and end. For example, if the largest radius of transition at the leading edge of a carrier's lobe is 6.0 mm then the smallest radius of transition at an adjoining valley should be 2.0 mm or less.

While the location of the passageways through the porous ceramic body may not be critical in some applications, providing a plurality of passageways symmetrically spaced around the end of the body, such that the distances from a passageway to the closest surface of the wall is minimized and standardized, may facilitate preparation of the catalyst by minimizing the amount of time needed to diffuse liquid used in the catalyst preparation process into and through the carrier. The shape of all the passageways may be identical or, as shown in FIG. 1, the passageways may have different shapes.

Figure 3:
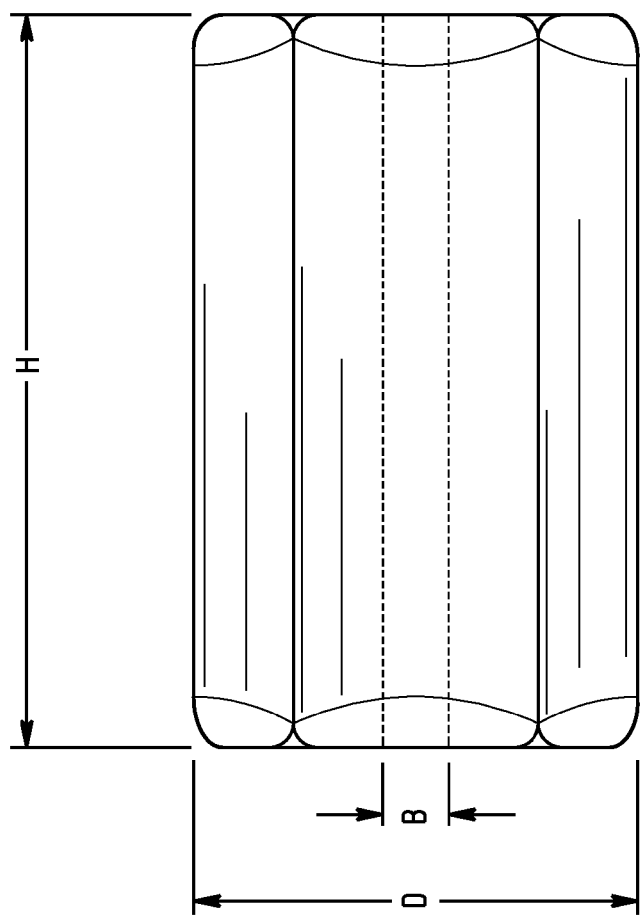
FIG. 3 is a side view of a the carrier shown in FIG. 2.
Figure 2:
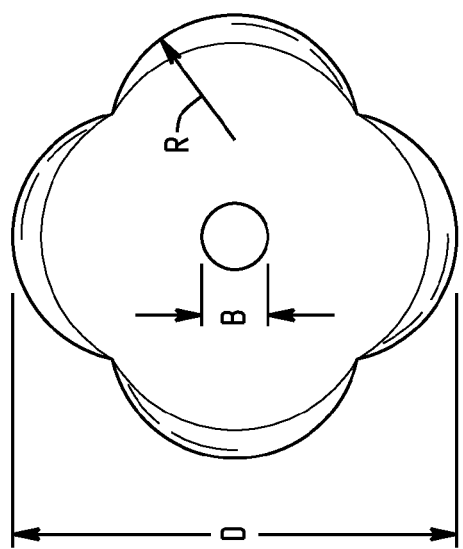
FIG. 2 is an end view of a second embodiment of a carrier of this invention.

Shown in FIGS. 2 and 3 are an end view and a side view, respectively, of a quadrilobal catalyst that contains a passageway therethrough. The passageway has an inside diameter B. The catalyst contains four round lobes. D refers to the diameter of the overall catalyst. R refers to the radius of the individual round lobe. H refers to the height of the catalyst. In one embodiment, the present invention may be a catalyst comprising silver and promoters useful for the epoxidation of olefins deposited on a multi-lobal shaped carrier having between 3 and 8 lobes with a geometric configuration wherein the ratio of D divided by R is between 3 and 8, and the ratio of H to D is between 0.5 and 3. It has been found particularly advantageous to use a shaped catalyst wherein the ratio of H to D is in the range of from 0.8 to 1.5. In FIG. 2, the overall diameter of the catalyst is approximately four times the radius of the individual lobes (R). The range of R is about 0.1 millimeters on the low side and nearly infinite or "flat" on the high side. Preferably R is about 1 to 20 millimeters; more preferably about 1 to 10 millimeters. The overall diameter D of the catalyst is preferably between 2 and 50 millimeters; most preferably between about 4 and 20 millimeters. The range for H is about 2 to 50 millimeters; preferably about 4 to 20 millimeters; preferably the ratio of H to D is about 1 to 1. The diameter (bore size) of hole B varies from 0.5 to about 5 millimeters, preferably between about 1 and about 4 millimeters. The bore size may be between about 0.1 to 0.9 times the diameter (D) of the catalyst; preferably between about 0.2 and 0.6 times the diameter of the catalyst. While only one hole is shown in FIG. 3, it is contemplated that one or more passageways may be employed. In a preferred embodiment, there is one passageway for each lobe.

Figure 4B:
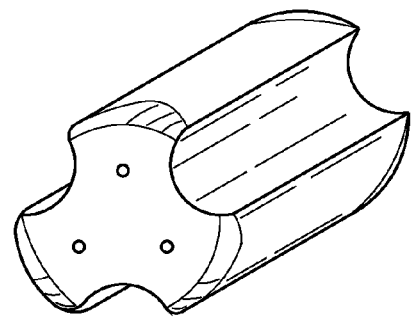

Shown in FIGS. 4A and 4B are an end view and a perspective view, respectively, of a three lobed carrier having three passageways.

Figure 5A:
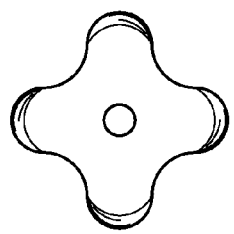
FIGS. 5A and 5B depict an end view and a perspective view of a fourth embodiment of a carrier of this invention.
Figure 5B:
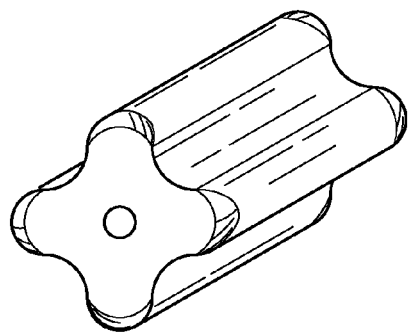

Shown in FIGS. 5A and 5B are an end view and a perspective view, respectively, of a four lobed carrier having a single passageway.

Figure 6A:
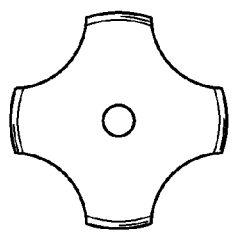
FIGS. 6A and 6B depict an end view and a perspective view of a fifth embodiment of a carrier of this invention.
Figure 6B:
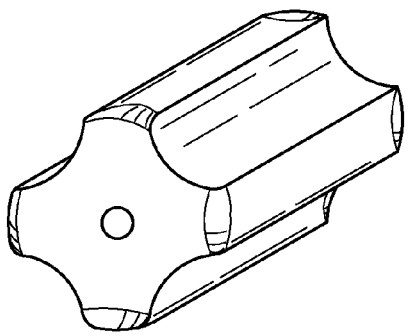

Shown in FIGS. 6A and 6B are an end view and a perspective view, respectively, of another four lobed carrier having a single passageway.

Figure 7:
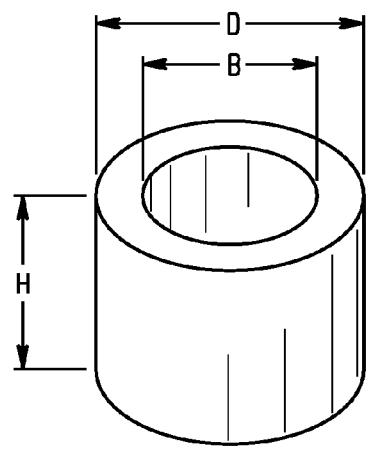
FIG. 7 depicts a conventional ring shaped carrier and is labeled Prior Art; to and FIGS. 8A-8J depict cross-sectional views of ten carriers of this invention.
Figure 8A:
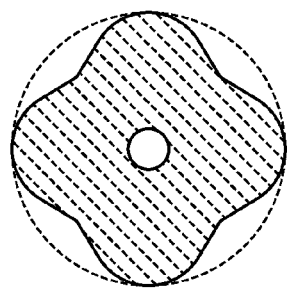
Figure 8F:
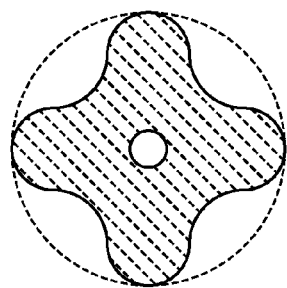
Figure 8B:
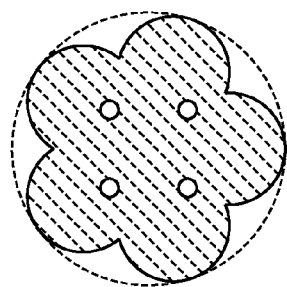
Figure 8G:
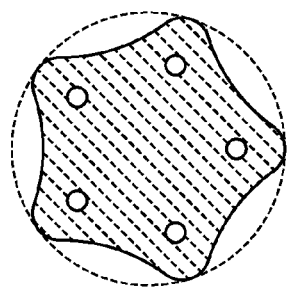
Figure 8C:
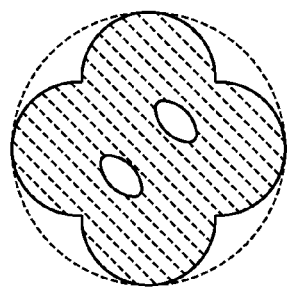
Figure 8H:
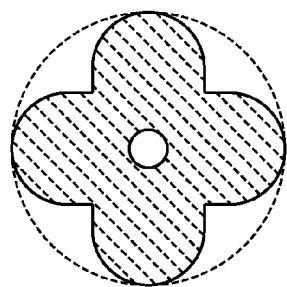
Figure 8D:
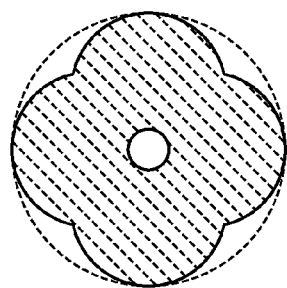
Figure 8I:
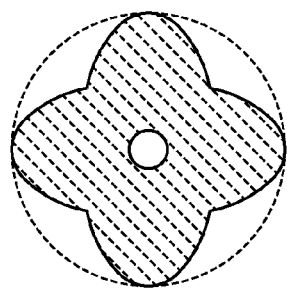
Figure 8E:
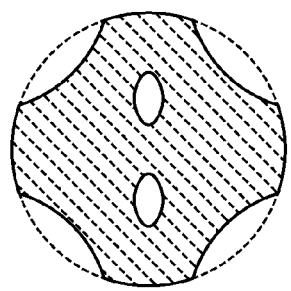
Figure 8J:
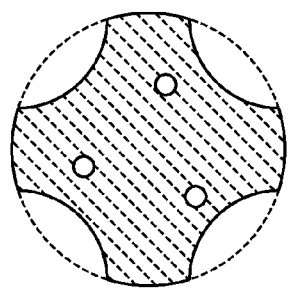

FIG. 7 is a perspective view of a prior art carrier that has no lobes and the corners of the carrier are not rounded.

FIGS. 8A through 8J disclose cross-sectional views of several multi-lobed carriers having at least three lobes and between one and five passageways. The shape designated A has four truncated lobes and two oval shaped passageways. The shape designated B has four lobes and a gradual rounded intersection of the lobes. The shape designated C has four semi-circular lobes. The shape designated D has five semi-circular lobes. The shape designated E has four lobes and a gradual rounded intersection of the lobes. The shape designated F has four truncated lobes and three passageways. The shape designated G has four extended lobes. The shape designated H has four extended semi-circular lobes. The shape designated I has five lobes and a rounded intersection of the lobes. The shape designated J has four semi-circular lobes including a rounded intersection of the lobes.

Typical prior art preparation of an alpha alumina carrier involves mixing alpha alumina powder(s) with a combination of bonding agents, extrusion aids, water, fluxing agents, other alumina materials and optionally, burnout materials to provide a manually malleable mixture. Detailed descriptions of processes that can be used to make suitable mixtures can be found in U.S. Pat. No. 6,831,037 and U.S. Pat. No. 7,825,062. A suitable mixture may then be extruded through an appropriately shaped die to provide an extrudate having three or more lobes formed in the wall of the extrudate and parallel to the central axis of extrusion. The extruate may then be cut into a plurality of individual unfired, carrier precursors commonly known as greenware. The extrudate may be cut by a fast moving blade which cuts through the extrudate essentially perpendicular to the direction of extrusion. The resulting carrier precursors have a first end, a second end and the wall which extends between the first end and the second end. The ends are essentially parallel to one another and perpendicular to the wall. The first end and wall intersect at a right angle which inherently defines a small, uniform radius of transition. The radius of transition defines a circumferential line which has a uniform radius of transition. Similarly, the second end and wall intersect at a right angle which inherently defines a small, uniform radius of transition that is equal to the radius of transition at the intersection of the first end and wall. A plurality of the carrier precursors may then be tumbled in a container, such as a rotating tube, that allows the precursors to contact one another and/or the sides of the container. During the tumbling process, the carrier precursors contact one another and the leading edges of the lobes are compressed thereby rounding the edges of the lobes. Due to the multi-lobe design of the precursor, the leading edge of the precursor is compressed the greatest amount and the valleys between the lobes are not compressed or are compressed very little. Consequently, the leading edges of the lobes have the largest radius of transition and the valleys between the lobes have the smallest radius of transition. Between the leading edge of a lobe and the valley, the precursor's radius of transition may be larger than the smallest radius of transition but smaller than the largest radius of transition. The amount that the leading edge is compressed, and thus the leading edge's radius of transition, may be controlled by adjusting factors such as the length of time the precursor is tumbled and the speed that the container is rotated. The precursors having the non-uniform radius of transition are then dried to remove water and fired at high to temperatures to form the carrier body. High temperatures (greater than 1200° C.) are required to affect the proper bonding of the alpha alumina particles to one another and to provide a carrier having the desired surface area. Instead of using an extrusion process to form carriers of this invention, a suitable mixture may be disposed into a cavity and the carrier may be formed by pressing the mixture to the desired shaped. Carriers that have been formed by pressing may be manufactured with the desired rounding at the carrier's end to wall interfaces and therefore do not need to tumbled in order to impart the desired non-uniform radius of transition at the intersections of the carrier's ends and wall.

A carrier of this invention may be made from any porous refractory material that is relatively inert in the presence of ethylene oxidation feeds, products and reaction conditions provided such material has the desired physical and chemical properties. Generally, the material comprises an inorganic material, in particular an oxide, which can include, for example, alumina, silicon carbide, carbon, silica, zirconia, magnesia, silica-alumina, silica-magnesia, silica-titania, alumina-titania, alumina-magnesia, alumina-zirconia, thoria, silica-titania-zirconia and various clays.

The preferred porous refractory material comprises alumina preferably of a high purity of at least 90 weight percent alumina and, more preferably, at least 98 weight percent alumina. Frequently, the refractory material comprises at most 99.9 weight percent, more frequently at most 99.5 weight percent alumina. Among the various available forms of alumina, alpha-alumina is the most preferred.

After firing, the carrier's micro physical characteristics may have a mean pore diameter of 0.3 to 15 µm, preferably 1 to 10 µm; and a monomodal, bimodal or multimodal pore size distribution as determined by mercury intrusion to a pressure of $3.0 \times 10^8$ Pa using a Micrometrics Autopore 9200 model (130° contact angle, mercury with a surface tension of 0.473 N/m, and correction for mercury compression applied). The following are some of the many options for carrier pore distribution. First, the carrier may have a surface area of at least 1 $m^2/g$, and to a pore size distribution such that pores with diameters in the range of from 0.2 to 10 µm represent at least 70% of the total pore volume and such pores together provide a pore volume of at least 0.27 ml/g, relative to the weight of the carrier. Second, a carrier may have a median pore diameter of more than 0.5 µm, and a pore size distribution wherein at least 80% of the total pore volume is contained in pores with diameters in the range of from 0.1 to 10 µm and at least 80% of the pore volume contained in the pores with diameters in the range of from 0.1 to 10 µm is contained in pores with diameters in the range of from 0.3 to 10 µm. Third, a carrier having at least two log differential pore volume distribution peaks in a pore diameter range of 0.01-100 µm and at least one peak of the above peaks is present in a pore diameter range of 0.01-1.0 µm in the pore size distribution measured by mercury intrusion, wherein each peak is a maximum value of the log differential pore volume distribution of 0.2 $cm^3/g$ or larger. Fourth, a carrier having a bimodal pore size distribution, with a first mode of pores which has a mean diameter ranging from about 0.01 m to about 5 µm, and a second mode of pores which has a mean diameter ranging from about 5 µm to about 30 µm. Fifth, a carrier having a pore volume from pores with less than 1 micron in diameter of less than 0.20 ml/g, a pore volume from pores with greater than 5 micron in diameter of less than 0.20 ml/g, and a pore volume from pores between 1 micron in diameter and 5 microns in diameter at least 40 percent of a total pore volume. Furthermore, the surface area of the carrier, as measured by the B.E.T. method, can be in the range of from 0.03 $m^2/g$ to 10 $m^2/g$, preferably from 0.05 $m^2/g$ to 5 $m^2/g$ and most preferably from 0.1 $m^2/g$ to 3 $m^2/g$. Suitably, the surface area is at least 0.5 $m^2/g$. The B.E.T. method of measuring surface area has been described in detail by Brunauer, Emmet and Teller in J. Am. Chem. Soc. 60 (1938) 309-316, which is incorporated herein by reference.

In addition to the carrier having a specific geometric configuration, incorporated onto the carrier is at least a catalytically effective amount of silver and, optionally, one or more promoters and, optionally, one or more co-promoters. Thus, the inventive catalyst comprises a carrier, a catalytically effective amount of to silver and, optionally, one or more promoters and, optionally, one or more co-promoters.

In general, a catalyst of the present invention may be prepared by impregnating a carrier of this invention with silver and, optionally, one or more promoters, such as, for example, rare earth metals, magnesium, rhenium and alkali metals (lithium, sodium, potassium, rubidium and cesium), or compounds thereof, and, optionally, one or more co-promoters, such as, for example, sulfur, molybdenum, tungsten and chromium, or compounds thereof. Among the promoter components that can be incorporated into the carrier, rhenium and the alkali metals, in particular, the higher alkali metals, such as potassium, rubidium and cesium, are preferred. Most preferred among the higher alkali metals is cesium, which may be used alone or in a mixture together with for example potassium and/or lithium. Either the rhenium promoter may be used without an alkali metal promoter being present or an alkali metal promoter may be used without a rhenium promoter being present or a rhenium promoter and an alkali metal promoter can both be present in the catalyst system. The co-promoters for use in combination with rhenium can include sulfur, molybdenum, tungsten, and chromium.

Silver is incorporated into the carrier by contacting it with a silver solution formed by dissolving a silver salt, or silver compound, or silver complex in a suitable solvent. The contacting or impregnation is preferably done in a single impregnation step whereby the silver is deposited onto the carrier so as to provide, for instance, at least about 8 weight percent silver up to about 30 weight percent, based on the total weight of the catalyst. In another preferred embodiment a substantially higher amount of silver is deposited onto the carrier, for instance, at least 12 weight percent silver, based on the total weight of the catalyst, where the silver may be deposited in more than one impregnation step, for example in two, three or four impregnation steps.

The one or more promoters can also be deposited on the carrier either prior to, coincidentally with, or subsequent to the deposition of the silver, but, to preferably, the one or more promoters are deposited on the carrier coincidentally or simultaneously with the silver. When the catalyst comprises silver, rhenium and a co-promoter for rhenium, it may be advantageous to deposit the co-promoter prior to or simultaneous with the deposition of silver, and to deposit rhenium after at least a portion of the silver has been deposited. The advantage is this sequence of deposition steps materializes in an enhanced stability of the catalyst in particular in respect of its activity.

Promoting amounts of alkali metal or mixtures of alkali metal can be deposited on a carrier using a suitable solution. Although alkali metals exist in a pure metallic state, they are not suitable for use in that form. They are generally used as compounds of the alkali metals dissolved in a suitable solvent for impregnation purposes. The carrier may be impregnated with a solution of the alkali metal compound(s) before, during or after impregnation of the silver in a suitable form has taken place. An alkali metal promoter may even be deposited on the carrier after the silver component has been reduced to metallic silver.

The promoting amount of alkali metal utilized will depend on several variables, such as, for example, the surface area and pore structure and surface chemical properties of the carrier used, the silver content of the catalyst and the particular ions and their amounts used in conjunction with the alkali metal cation.

The amount of alkali metal promoter deposited upon the carrier or present on the catalyst is generally in the range of from about 10 parts per million to about 3000 parts per million, preferably between about 15 parts per million and about 2000 parts per million and more preferably, between about 20 parts per million and about 1500 parts per million, by weight of the metal relative to the weight of total catalyst.

The carrier can also be impregnated with rhenium ions, salt(s), compound(s), and/or complex(es). This may be done at the same time that the alkali metal promoter is added, or before or later; or at the same time that the silver is added, or before or later. Rhenium, alkali metal, and silver may be in the same impregnation solution. Their presence in different solutions will provide suitable catalysts, and in some instances even improved catalysts.

The preferred amount of rhenium, calculated as the metal, deposited on or present on the shaped agglomerate or catalyst ranges from about 0.1 micromoles ($\mu$mole) per gram to about 10 micromoles per gram, more preferably from about 0.2 micromoles per gram to about 5 micromoles per gram of total catalyst, or, alternatively stated, from about 19 parts per million to about 1860 parts per million, preferably from about 37 parts per million to about 930 parts per million by weight of total catalyst. The references to the amount of rhenium present on the catalyst are expressed as the metal, irrespective of the form in which the rhenium is actually present.

The rhenium compound used in the preparation of the instant catalyst includes rhenium compounds that can be solubilized in an appropriate solvent. Preferably, the solvent is a water-containing solvent. More preferably, the solvent is the same solvent used to deposit the silver and the alkali metal promoter.

Examples of suitable rhenium compounds used in making the inventive catalyst include the rhenium salts such as the rhenium halides, the rhenium oxyhalides, the rhenates, the perrhenates, the oxides and the acids of rhenium. A preferred compound for use in the impregnation solution is the perrhenate, preferably ammonium perrhenate. However, the alkali metal perrhenates, alkaline earth metal perrhenates, silver perrhenates, other perrhenates and rhenium heptoxide can also be suitably utilized.

The one or more co-promoters can be deposited on the carrier by any suitable manner known to those skilled in the art. The co-promoter is deposited on the carrier either prior to, coincidentally with, or subsequent to the deposition of the silver, but preferably, the one or more co-promoters are deposited on the carrier coincidentally or simultaneously with the silver. A co-promoting amount of co-promoter is deposited on the carrier and can generally be in the range of from about 0.01 to about 25, or more, moles per gram of total catalyst.

The catalysts according to the present invention have a particularly high activity and high selectivity for ethylene oxide production in the direct oxidation of ethylene with molecular oxygen to ethylene oxide. For instance, the inventive catalyst can have an initial selectivity of at least about 86.5 mole percent, preferably, at least 87 mole percent and, most preferably, at least 88.5 mole percent. It is a benefit of this invention that when packing the inventive catalyst into a catalyst bed it provides a catalyst bed having a relatively high silver loading, without causing an increased pressure drop over the catalyst bed when in use in the process for manufacturing ethylene oxide, and/or having an improved balance of packing density relative to such pressure drop. When decreasing the bore diameter, the balance of pressure drop/packing density behaves favorably in a typical reactor tube used in the manufacture of ethylene oxide, compared with predictions on the basis of theoretical models, for example the Ergun Correlation, see W. J. Beek and K. M. K. Muttzall, "Transport Phenomena", J. Wiley and Sons Ltd, 1975, p. 114. By practicing the present invention, it is achievable that the silver loading of the catalyst may be at least 150 kg silver/$m^3$ catalyst bed, preferably at least 170 kg silver/$m^3$ catalyst bed, more preferably at least 200 kg silver/$m^3$ catalyst bed, and in particular at least 250 kg silver/$m^3$ catalyst bed. Frequently, the silver loading is at most 800 kg silver/$m^3$ catalyst bed, more frequently at most 600 kg silver/$m^3$ catalyst bed, still more frequently at most 550 kg silver/$m^3$ catalyst bed. The high silver loading permits the application of relatively mild conditions in the process for manufacturing ethylene oxide, in particular temperature, for the achievement of a given work rate, along with the achievement of an improved selectivity and catalyst life, in particular in terms of activity stability and selectivity stability.

As it is used herein with reference to the selectivity of a catalyst, the term "selectivity", $S_w$, means the mole percent (%) of the desired ethylene oxide formed relative to the total of ethylene converted. The selectivity may be specified at a given work rate, w, for a catalyst with the work rate being defined as the amount of ethylene oxide produced per unit volume of catalyst (e.g., kg per m$^3$) per hour. As it is used herein with reference to the activity of a catalyst, the term "activity", Tw, means the temperature needed to reach a given work rate.

The conditions for carrying out the epoxidation reaction in the presence of the catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1,2-dichloroethane, vinyl chloride, ethyl chloride or chlorinated polyphenyl compounds, to the desirability of employing recycle operations or applying successive conversions in different reactors to increase the yields of ethylene oxide, and to any other special conditions which may be selected in processes for preparing ethylene oxide. Pressures in the range of from atmospheric to about 3450 kPa gauge (500 psig) are generally employed. Higher pressures, however, are not excluded. The molecular oxygen employed as reactant can be obtained from any suitable source including conventional sources. A suitable oxygen charge can include relatively pure oxygen, or a concentrated oxygen stream comprising oxygen in major amount with lesser amounts of one or more diluents, such as nitrogen and argon, or any other oxygen-containing stream, such as air. The use of the present catalysts in ethylene oxide reactions is in no way limited to the use of specific conditions among those that are known to be effective.

For purposes of illustration only, the following table shows the range of conditions that are often used in current commercial ethylene oxide reactor units:

TABLE I

| | |
|---|---|
| *GHSV | 1500-10,000 |
| Inlet Pressure | 150-400 psig |
| Ethylene Oxide (EO) Production (Work Rate) | 2-20 lbs. EO/cu. ft. catalyst/hr. |
| Coolant temperature | 180-315° C. |
| Catalyst temperature | 180-325° C. |
| O2 conversion level | 10-60% |
| Inlet Feed | |
| Ethylene | 1-40% |
| Oxygen | 3-12% |
| Carbon dioxide | 0-15% |
| Ethane | 0-3% |
| Argon and/or methane and/or nitrogen | balance |
| Diluent chlorohydrocarbon moderator | 0.3-20 ppmv total |

*Cubic feet of gas at standard temperature and pressure passing over one cubic foot of packed catalyst per hour.

In a preferred application, ethylene oxide is produced when an oxygen-containing gas is contacted with ethylene in the presence of the inventive catalysts under suitable epoxidation reaction conditions such as at a temperature in the to range of from about 180° C. to about 330° C., and, preferably, 200° C. to 325° C., and a pressure in the range of from atmospheric to about 3450 kPa gauge (500 psig) and, preferably, from 1034 kPa to 2758 kPa gauge (150 psig to 400 psig). In the normal practice of the process for manufacturing ethylene oxide, the feed stream which is contacted with the catalyst, and which comprises ethylene and oxygen, comprises in addition a low concentration of carbon dioxide, because carbon dioxide is a byproduct of the process and appears, in part, in the feed stream as a result of recycling. It is advantageous to reduce in the feed stream the concentration of carbon dioxide to a low level, as this will further enhance the catalyst performance in terms of activity, selectivity and catalyst life. It is preferred that the quantity of carbon dioxide in the feed is at most 4 mole-%, more preferred at most 2 mole-%, in particular at most 1 mole-%, relative to the total feed. Frequently the quantity of carbon dioxide will be at least 0.1 mole-%, more frequently at least 0.5 mole-%, relative to the total feed.

The ethylene oxide produced may be recovered from the reaction mixture to by using methods known in the art, for example by absorbing the ethylene oxide from the reactor outlet stream in water and optionally recovering the ethylene oxide from the aqueous solution by distillation.

The ethylene oxide produced in the epoxidation process may be converted into ethylene glycol, an ethylene glycol ether or an alkanolamine.

The conversion into the ethylene glycol or the ethylene glycol ether may comprise, for example, reacting the ethylene oxide with water, suitably using an acidic or a basic catalyst. For example, for making predominantly the ethylene glycol and less ethylene glycol ether, the ethylene oxide may be reacted with a ten fold molar excess of water, in a liquid phase reaction in presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. If the proportion of water is lowered the proportion of ethylene glycol ethers in the reaction mixture is increased. The ethylene glycol ethers thus produced may be a di-ether, tri-ether, tetra-ether or a subsequent ether. Alternative ethylene glycol ethers may be prepared by converting the ethylene oxide with an alcohol, in particular a primary alcohol, such as methanol or ethanol, by replacing at least a portion of the water by the alcohol.

The conversion into the alkanolamine may comprise reacting ethylene oxide with an amine, such as ammonia, an alkyl amine or a dialkylamine. Anhydrous or aqueous ammonia may be used. Anhydrous ammonia is typically used to favor the production of monoalkanolamine. For methods applicable in the conversion of ethylene oxide into the alkanolamine, reference may be made to, for example U.S. Pat. No. 4,845,296, which is incorporated herein by reference.

Ethylene glycol and ethylene glycol ethers may be used in a large variety of industrial applications, for example in the fields of food, beverages, tobacco, cosmetics, thermoplastic polymers, curable resin systems, detergents, heat transfer systems, etc Alkanolamines may be used, for example, in the treating ("sweetening") of natural gas.

The above description is considered that of particular embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the Doctrine of Equivalents.

What is claimed is:

1. A porous ceramic body, comprising: a first end; a second end; and a wall disposed between and intersecting said ends, said wall comprising at least three lobes and at least three valleys formed in the length of the wall, each valley located between two of said lobes, said lobes rounded at the intersection of said first end and said wall, and said valleys not rounded at the intersection of said first end and said wall.

2. The porous ceramic body of claim 1 further comprising at least one passageway disposed within said wall between said ends.

3. The porous ceramic body of claim 2 wherein said at least one passageway has a non-circular cross-sectional shape.

4. The porous ceramic body of claim 3 wherein said non-circular cross-sectional shape is selected from the group consisting oval, rectangular and polygonal.

5. The porous ceramic body of claim 1 further comprising at least three passageways disposed within said wall between said ends.

6. The porous ceramic body of claim 5 wherein said wall comprises no more than eight lobes.

7. The porous ceramic body of claim 6 comprises an equal number of lobes and passageways.

8. The porous ceramic body of claim 5 comprises at least four lobes and no more than six lobes.

9. The porous ceramic body of claim 6 comprises an unequal number of lobes and passageways.

10. The porous ceramic body of claim 9 comprises an even number of lobes and an odd number of passageways.

11. The porous ceramic body of claim 9 comprises an odd number of lobes and an even number of passageways.

12. The porous ceramic body of claim 1 wherein said lobes are rounded at the intersection of said second end and said wall, and valleys are not rounded at the intersection of said second end and said wall.

13. The porous ceramic body of claim 1, wherein each lobe has a radius R, the overall diameter of said ceramic body is D, the ratio of D to R is between 1 and 8, the height of said ceramic body is H, and the ratio of H to D is between 0.5 and 3.

14. The porous ceramic body of claim 13, wherein the diameter D of the porous ceramic body is between 4 and 18 millimeters, the radius R of a lobe is between 1 and 20 millimeters, the ratio of D to R is between 3 and 8 and the height H of the ceramic body is between 4 and 18 millimeters.

15. The porous ceramic body of claim 1 has a surface area between 0.03 $m^2/g$ to 10 $m^2/g$.

16. The porous ceramic body of claim 1 has a median pore diameter of more than 0.5 μm, a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.

17. The porous ceramic body of claim 1 comprising a pore size distribution having at least two log differential pore volume distribution peaks in a pore diameter range of 0.01-100 μm and at least one peak of the above peaks is present in a pore diameter range of 0.01-1.0 μm in the pore size distribution measured by mercury intrusion, wherein each peak is a maximum value of the log differential pore volume distribution of 0.2 $cm^3/g$ or larger.

18. The porous ceramic body of claim 1 has a bimodal pore size distribution, with a first mode of pores which has a mean diameter ranging from about 0.01 μm to about 5 μm, and a second mode of pores which has a mean diameter ranging from about 5 μm to about 30 μm.

19. The porous ceramic body of claim 1 has a pore volume from pores with less than 1 micron in diameter of less than 0.20 ml/g, a pore volume from pores with greater than 5 micron in diameter of less than 0.20 ml/g, and a pore volume from pores between 1 micron in diameter and 5 microns in diameter at least 40 percent of a total pore volume.

20. A catalyst comprising the porous ceramic body of claim 1, silver and one or more promoters useful for the epoxidation of olefins.

21. The catalyst of claim 20 wherein silver is present in a quantity in the range between 10 and 30 weight percent of the total weight of the catalyst.

22. The catalyst of claim 20 wherein one or more promoter components is selected from the group consisting of rare earth metals, magnesium, rhenium; and alkali metals.

23. The catalyst of claim 22 wherein the quantity of said rhenium promoter is at least 1.25 mmole/kg, relative to the total weight of the catalyst.

24. The catalyst of claim 23 further comprising a rhenium co-promoter selected from the group consisting of sulfur, molybdenum, tungsten and chromium and wherein at least one of said alkali metals is selected from the group consisting of lithium, potassium, rubidium and cesium.

\* \* \* \* \*